US00PP37414P2

(12) United States Plant Patent
Kleinwee

(10) Patent No.: US PP37,414 P2
(45) Date of Patent: May 5, 2026

(54) ***CAMPANULA* PLANT NAMED 'CIPZ0011'**

(50) Latin Name: *Campanula interspecific*
Varietal Denomination: CIPZ0011

(71) Applicant: SYNGENTA CROP PROTECTION AG, Basel (CH)

(72) Inventor: Theodorus Cornelis Maria Van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/260,871

(22) Filed: Jul. 7, 2025

(51) Int. Cl.
*A01H 5/02* (2018.01)
*A01H 6/26* (2018.01)

(52) U.S. Cl.
USPC ..... Plt./414
CPC ..... *A01H 6/264* (2018.05); *A01H 5/02* (2013.01)

(58) Field of Classification Search
USPC ..... Plt./414
CPC ..... A01H 6/264; A01H 5/02
See application file for complete search history.

*Primary Examiner* — Keith O. Robinson
(74) *Attorney, Agent, or Firm* — Dale Skalla

(57) ABSTRACT

A new garden type *Campanula* plant named 'CIPZ0011' particularly distinguished by its medium vigor, mounded to upright plant habit, a large size flower with blue flower color, and its flowering in June in moderate climate conditions.

1 Drawing Sheet

Figure 1:
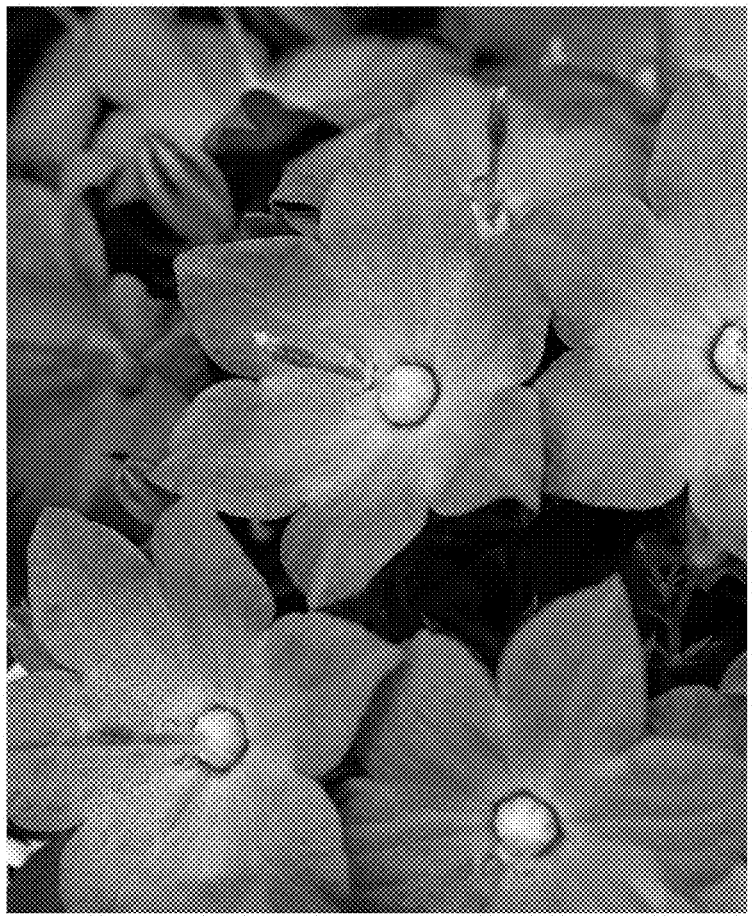

Latin name of the genus and species of the plant claimed: *Campanula interspecific.*

Varietal denomination: 'CIPZ0011'.

BACKGROUND OF THE NEW PLANT

The present invention comprises a new *Campanula,* botanically known as *Campanula interspecific* and hereinafter referred to by the variety name 'CIPZ0011'.

'CIPZ0011' is a product of a planned breeding program. The new cultivar is medium vigorous, has a mounded to upright plant habit, a large size flower with blue flower color, and is flowering in June in moderate climate conditions.

'CIPZ0011' originated from a cross made in June 2017 in Enkhuizen, The Netherlands. Seeds were sown in February 2018 in Enkhuizen, The Netherlands and 'CIPZ0011' was selected from the resulting population in June 2018 in Enkhuizen, The Netherlands.

The female parent was the proprietary seedling 'PERAV1814-2', not patented.

TABLE 1

Characteristics of the female parent, compared to 'CIPZ0011':

| | 'CIPZ0011' | 'PERAV1814-2' |
|---|---|---|
| Flowering time: | June | About 2 weeks earlier |
| Flower color: | Blue, light blue at center | Blue margin with white center |
| Fertility: | Male sterile (degenerated anthers) | Somewhat male fertile (normal developed anthers) |

The male parent was the proprietary seedling 'CY-0022-4.25', not patented.

TABLE 2

Characteristics of the male parent, compared to 'CIPZ0011':

| | 'CIPZ0011' | 'CY-0022-4.25' |
|---|---|---|
| Flower size: | Big | Medium size |
| Plant habit: | Mounding to upright | Mounding to semi-trailing |
| Fertility: | Male sterile (degenerated anthers) | Somewhat male fertile (normal developed anthers) |

The first act of asexual reproduction of 'CIPZ0011' was accomplished when vegetative stem cuttings were propagated from the initial selection in September 2018 in Enkhuizen, The Netherlands.

BRIEF SUMMARY OF INVENTION

Horticultural examination of plants grown from cuttings of the plant initiated in September 2018 and continuing thereafter, has demonstrated that the combination of characteristics as herein disclosed for 'CIPZ0011' are firmly fixed and are retained through successive generations of asexual reproduction.

'CIPZ0011' has not been observed under all possible environmental conditions. The phenotype may vary significantly with variations in environment such as temperature, light intensity and day length.

A Plant Breeder's Right for this cultivar has not yet been applied for. 'CIPZ0011' has not been made publicly available prior to the effective filing date of this application, notwithstanding any disclosure that may have been made less than one year prior to the effective filing date of this application by the inventor or another who obtained 'CIPZ0011' directly from the inventor.

The following traits have been repeatedly observed and are determined to be basic characteristics of the new variety.

The combination of these characteristics distinguishes this *Campanula* as a new and distinct variety.

BRIEF DESCRIPTION OF THE PHOTOGRAPHS

The accompanying photographic drawing shows typical flower and foliage characteristics of 'CIPZ0011' with colors being as true as possible with an illustration of this type.

Figure 2:
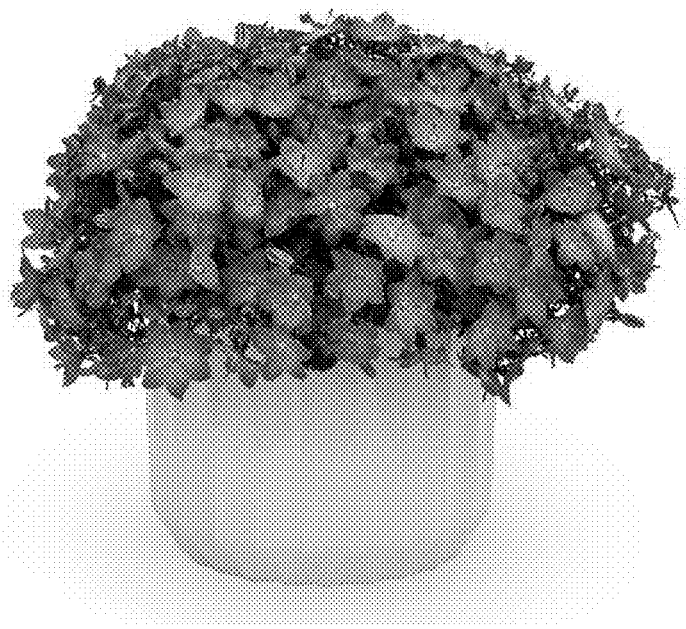

The photographic drawing shows in FIG. 1 a close view of flower of the new variety and in FIG. 2 a flowering plant from an indoor trial.

The aforementioned photographs: FIG. 1, as well as FIG. 2 were taken on May 26, 2025 and Jun. 2, 2025, respectively. Both photographs were taken from a plant from the same outdoor trial in Gilroy, California, USA.

These plants were about 21 weeks of age. One rooted cutting per pot had been planted in a 15 cm pot, not pinched.

The measurements were taken in Enkhuizen, The Netherlands, in June 2025 on 13-week-old plants from an outdoor trial.

DETAILED BOTANICAL DESCRIPTION

Color references are made to The Royal Horticultural Society Colour Chart (R.H.S.) 2001.

TABLE 3

DIFFERENCES BETWEEN THE NEW VARIETY 'CIPZ0011' AND A MOST SIMILAR VARIETY:

| | 'CIPZ0011' | 'Mirabell Heavenly Blue', Not patented |
|---|---|---|
| Flower size: | Big | Medium |
| Habit: | Mounding to upright | Semi trailing |
| Branching: | Moderate branching | Very dense branching |

Plant:

*Form, growth and habit*.—Hardy Perennial (can endure −20° C.). medium to low vigor, mounding to upright habit, moderate branching.

*Plant height* (*above soil*).—16 cm.

*Plant height* (*inflorescence included*).—19 cm.

*Plant width*.—19 cm.

Roots:

*Number of days to initiate roots*.—About 11 days at about 22° C.

*Number of days to produce a rooted cutting*.—18-20 days at 20° C.

*Type*.—Fine, fibrous, moderate branching.

*Color*.—RHS 1D.

Foliage:

*Arrangement*.—Alternate, simple.

*Immature leaf, color upper surface*.—RHS 137A.

*Immature leaf, color lower surface*.—RHS 137D.

*Mature leaf, color, upper surface*.—RHS 139A.

*Mature leaf, color lower surface*.—RHS 137C.

*Length*.—4.5-5.5 cm on initial leaves, to 2.5-3.0 cm on leaves that develop near inflorescence.

*Width*.—3-3.5 cm on initial leaves, 1-1.5 cm on leaves that develop near inflorescence.

*Shape*.—Ovate on initial leaves to lanceolate on leaves near inflorescence.

*Base shape*.—Attenuate.

*Apex shape*.—Acute.

*Margin*.—Entire, occasionally dentated.

*Texture, upper surface*.—Glabrous.

*Texture, lower surface*.—Glabrous.

*Color of veins, upper surface*.—RHS 139C.

*Color of veins, lower surface*.—RHS 139C.

*Pattern of veining*.—Palmate.

*Petiole*.—Only present in initial leaves, up to 2.5 cm long. R.H.S. colour 39C. Width 2 mm. Glabrous surface.

Stem:

*Quantity of main branches per plant*.—About 30.

*Color of stem*.—RHS 146A.

*Length of stem*.—16 cm.

*Diameter*.—0.4 cm.

*Length of internodes*.—1.0-2.0 cm.

*Texture*.—Smooth.

*Color of peduncle*.—RHS 146B.

*Length of peduncle*.—3.0-5.0 cm.

*Peduncle diameter*.—0.3 cm.

*Texture*.—Smooth.

*Pedicel color*.—RHS 146B.

*Pedicel length*.—0.3-1.0 cm.

Inflorescence:

*Type*.—Single, sympetalous, campanulate.

*Quantity of inflorescences per plant*.—About 80 with clearly developed buds or flowers, many inflorescences in development.

*Lastingness of individual blooms on the plant*.—8-10 days.

*Fragrance*.—None.

Bud (when showing color):

*Color*.—RHS 1D.

*Length*.—2.0 cm.

*Width*.—1.0 cm.

*Shape*.—Elipsoid.

Immature inflorescence (at moment of opening):

*Diameter*.—4.0 cm.

*Color of ray florets, upper surface*.—RHS 93B towards margin, RHS 94C towards center.

*Color of ray florets, lower surface*.—RHS 94B.

Mature inflorescence:

*Diameter*.—4.5 cm.

*Depth of floret*.—2.0 cm.

*Diameter of floret*.—4.5 cm.

*Shape of corolla*.—6 petals; fused at base, and moderately diverging profile.

*Number of whorls of the corolla*.—One.

Ray florets:

*Average quantity of florets*.—40.

*Attitude of the flowers*.—Slightly outwards.

*Color of florets, upper surface*.—RHS 93B towards margin, RHS 94C towards center.

*Color lower surface*.—RHS 94B.

*Shape*.—Weakly reflexing ovate lobes, fused at base.

*Apex shape*.—Acute.

*Margin*.—Entire.

*Texture, upper surface*.—Papillate.

*Lower surface*.—Papillate.

Calyx:

*Type*.—6 strongly outward oriented lanceolate shaped sepals with acute apex, smooth surface and entire margin, fused at base.

*Length*.—1.0 cm.

*Width*.—2 mm.

*Color* (*both upper and lower*).—RHS 146B.

Reproductive organs:

*Pistil*.—One.

*Length*.—2.3 cm.

*Style color*.—RHS 92B near ovary, RHS 101C at middle, RHS 165B near stigma.

*Style length*.—1.8 cm.

*Stigma color*.—RHS 157D at the moment of spreading, RHS 138D when mature.

*Stigma shape*.—4-lobed.

*Ovary color*.—RHS 92D with stripes RHS 92C.

*Ovary length*.—0.5 cm.

*Ovary width*.—0.7 cm.

Androecium:

*Stamens*.—6, occasionally missing.

*Color of filaments*.—RHS N155D.

*Length filaments*.—0-0.2 cm.

*Anther color*.—RHS 164C.

*Anther length*.—0.1-0.3 cm.

*Anther shape*.—Linear, twisted.

*Color of pollen*.—No pollen observed.

*Fertility/seed set*.—Has not been determined to date.

*Disease/pest resistance*.—Has not been determined to date.

*Hardiness*.—Has proven to stand temperatures of −20° C.

What is claimed is:

1. A new and distinct variety of *Campanula* plant named 'CIPZ0011' substantially as illustrated and described herein.

* * * * *